US011282184B2

United States Patent
Kakishita et al.

(10) Patent No.: US 11,282,184 B2
(45) Date of Patent: Mar. 22, 2022

(54) APPARATUS, METHOD FOR DETERMINING STATE OF SAMPLE, AND ANALYSIS SYSTEM

(71) Applicant: HITACHI HIGH-TECHNOLOGIES CORPORATION, Tokyo (JP)

(72) Inventors: Yasuki Kakishita, Tokyo (JP); Hideharu Hattori, Tokyo (JP); Taku Sakazume, Tokyo (JP); Yoichiro Suzuki, Tokyo (JP)

(73) Assignee: HITACHI-HIGH-TECHNOLOGIES CORPORATION, Tokyo (JP)

( * ) Notice: Subject to any disclaimer, the term of this patent is extended or adjusted under 35 U.S.C. 154(b) by 171 days.

(21) Appl. No.: 16/635,502

(22) PCT Filed: May 31, 2018

(86) PCT No.: PCT/JP2018/020952
§ 371 (c)(1),
(2) Date: Jan. 30, 2020

(87) PCT Pub. No.: WO2019/026406
PCT Pub. Date: Feb. 7, 2019

(65) Prior Publication Data
US 2020/0242752 A1    Jul. 30, 2020

(30) Foreign Application Priority Data

Jul. 31, 2017    (JP) .............................. JP2017-147629

(51) Int. Cl.
*G06T 7/00*    (2017.01)
*G06N 20/00*    (2019.01)

(52) U.S. Cl.
CPC ........... *G06T 7/0004* (2013.01); *G06N 20/00* (2019.01)

(58) Field of Classification Search
CPC .............................. G06T 7/0004; G06T 7/00
See application file for complete search history.

(56) References Cited

U.S. PATENT DOCUMENTS

| | | | |
|---|---|---|---|
| 8,649,605 B2 * | 2/2014 | Franz ................. | G01N 21/9027 382/190 |
| 10,739,364 B2 * | 8/2020 | Satou ..................... | G01N 35/04 |

(Continued)

FOREIGN PATENT DOCUMENTS

| JP | 2007-309888 A | 11/2007 |
|---|---|---|
| JP | 2008-275473 A | 11/2008 |

(Continued)

OTHER PUBLICATIONS

Extended European Search Report dated Mar. 30, 2021 for European Patent Application No. 18840296.0.

(Continued)

*Primary Examiner* — Tuan H Nguyen
(74) *Attorney, Agent, or Firm* — Volpe Koenig

(57) ABSTRACT

A state of a sample surface is accurately determined without lowering analysis efficiency. There is provided an apparatus for determining a state of a sample to be analyzed contained in a container, in which the apparatus acquires an image of the sample, analyzes a position and a size of an object to be detected with respect to a detection range set in the image by using the image of the sample, and determines the state of the sample based on a result of the analysis.

14 Claims, 13 Drawing Sheets

(56) References Cited

U.S. PATENT DOCUMENTS

| | | |
|---|---|---|
| 2013/0315486 A1 | 11/2013 | Franz et al. |
| 2015/0339510 A1 | 11/2015 | Bolea et al. |
| 2018/0003728 A1 | 1/2018 | Yoshimichi et al. |

FOREIGN PATENT DOCUMENTS

| | | |
|---|---|---|
| JP | 2013-088114 A | 5/2013 |
| JP | 2014-500955 A | 1/2014 |
| JP | 2016-510211 A | 4/2016 |
| JP | 2016-85572 A | 5/2016 |
| JP | 5941692 B2 | 6/2016 |
| WO | 2012/066034 A1 | 5/2012 |
| WO | 2014/099644 A1 | 6/2014 |
| WO | 2016/121449 A1 | 8/2016 |

OTHER PUBLICATIONS

International Search Report for PCT/JP2018/020952, dated Aug. 7, 2018.

\* cited by examiner

[Fig. 1]
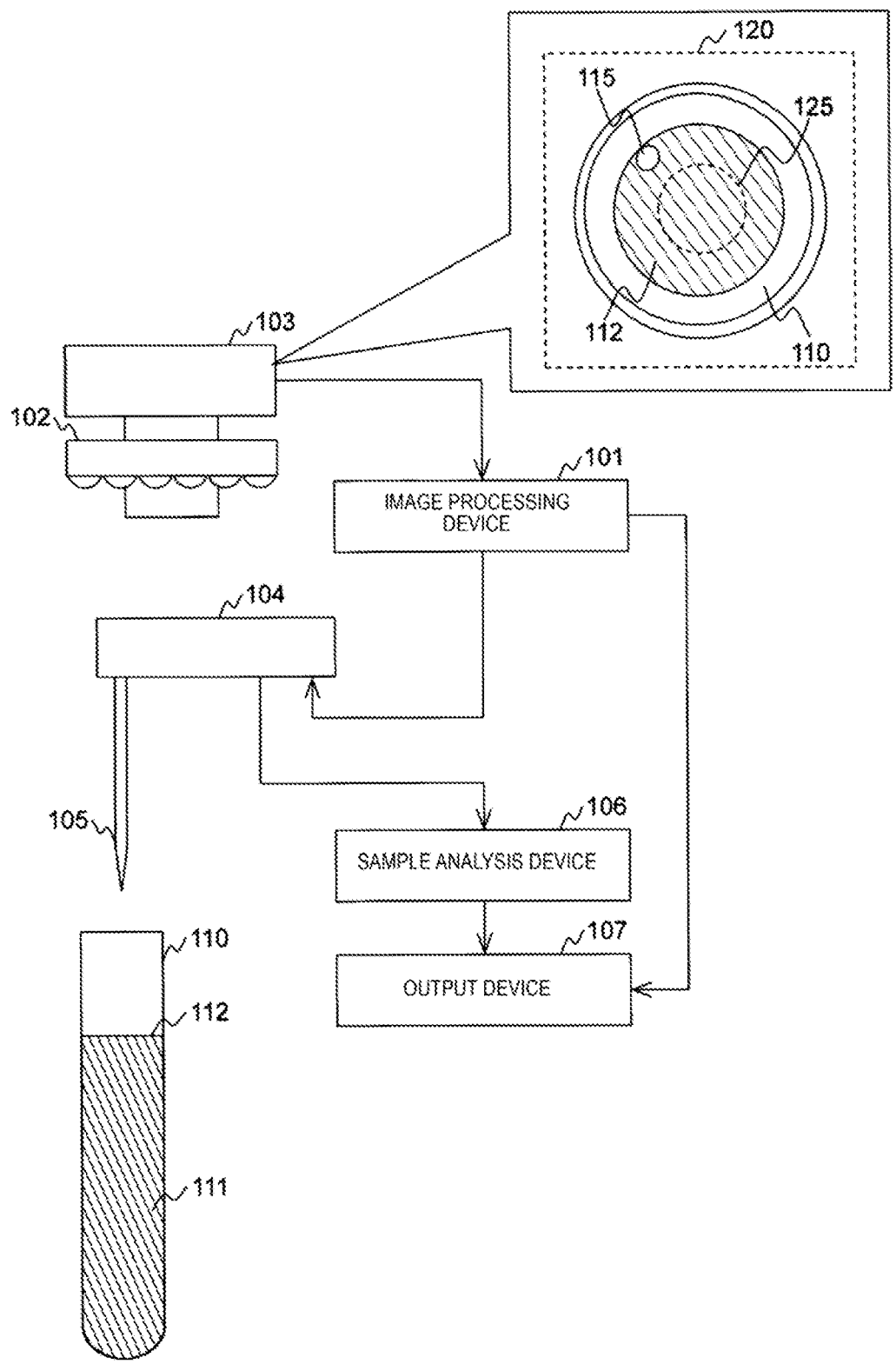

[Fig. 2]
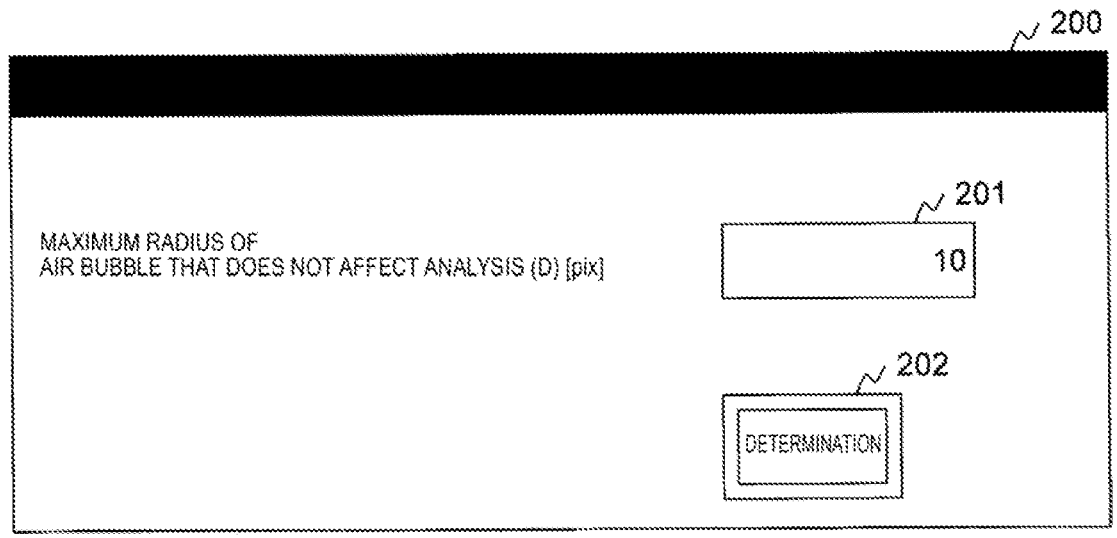
[Fig. 3A]
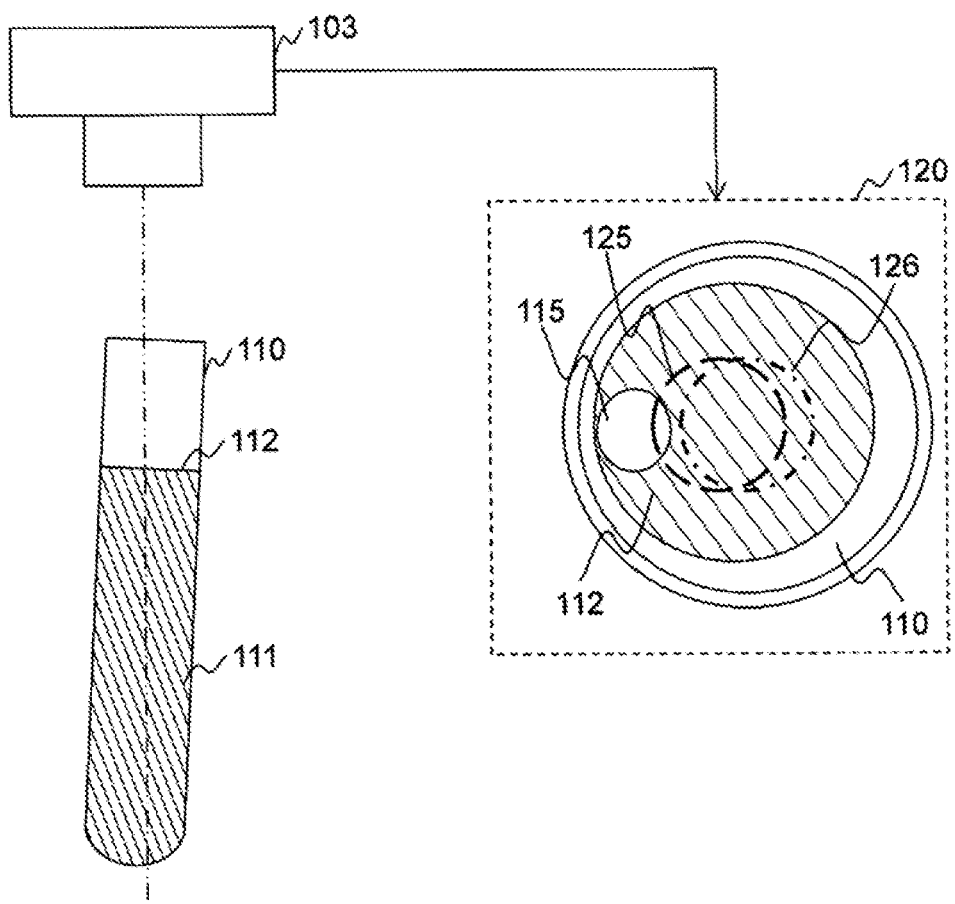

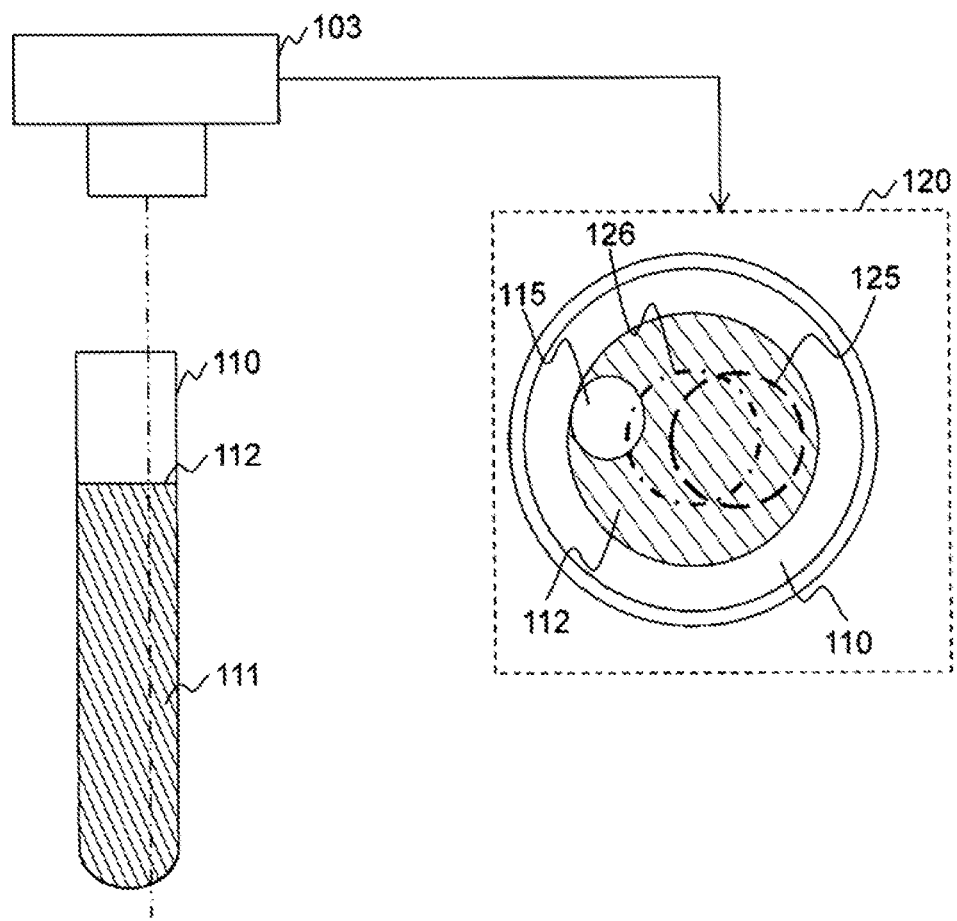
[Fig. 3B]

[Fig. 4]
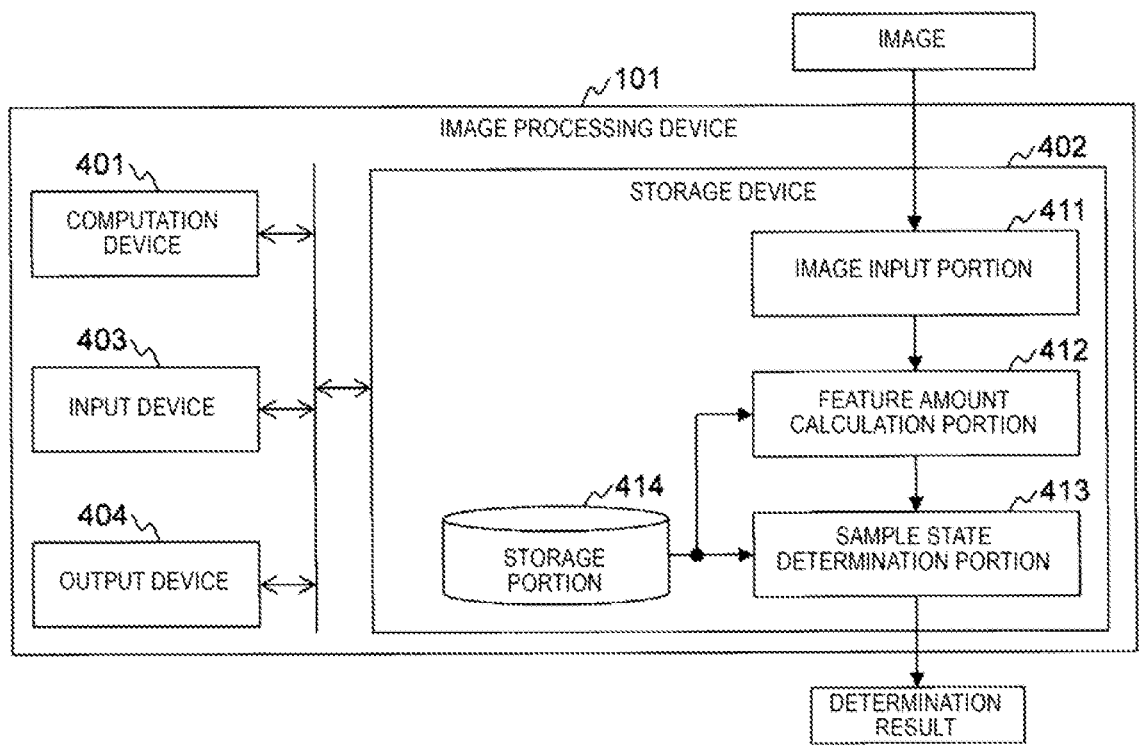

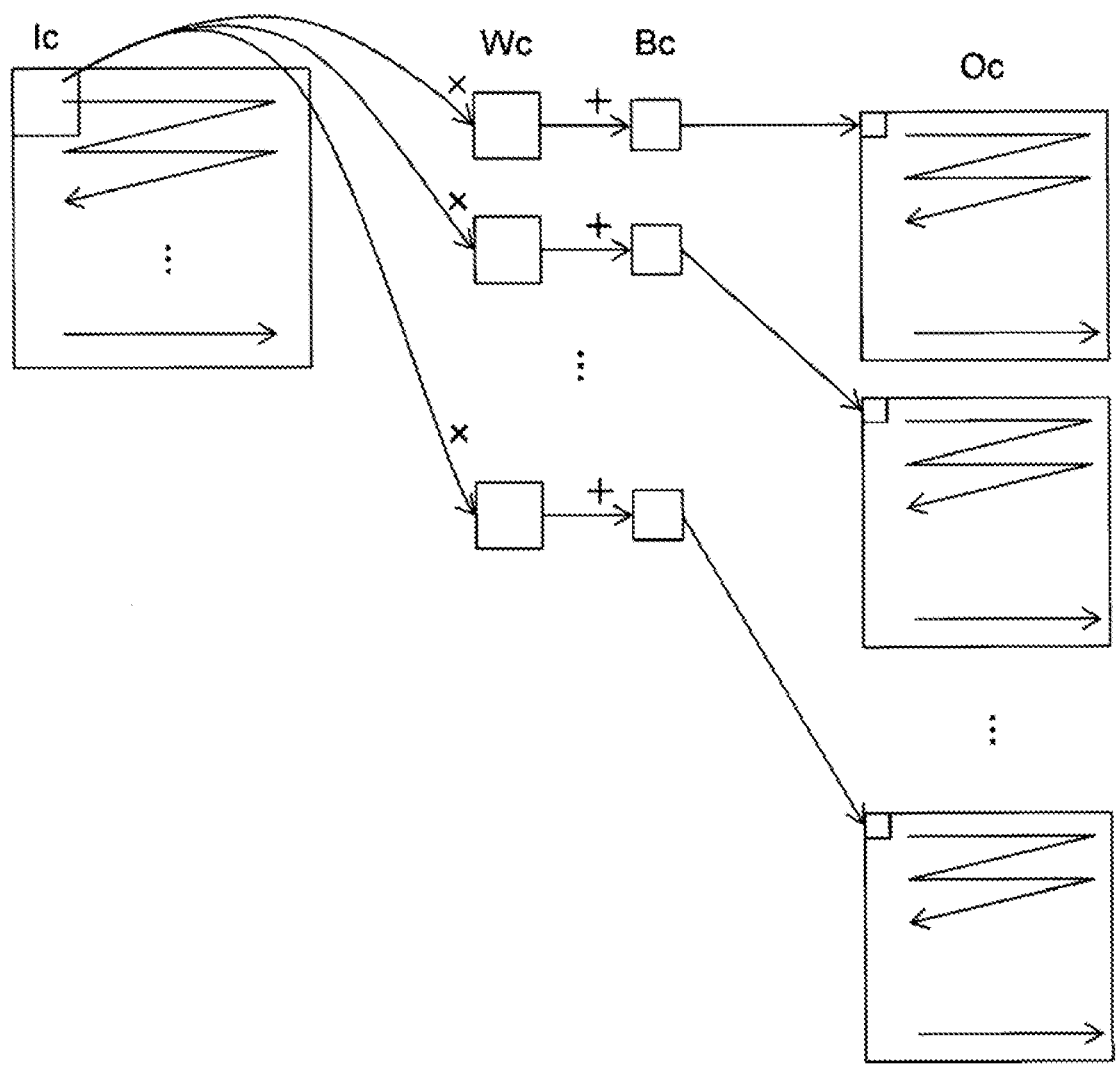
[Fig. 5]

[Fig. 6]
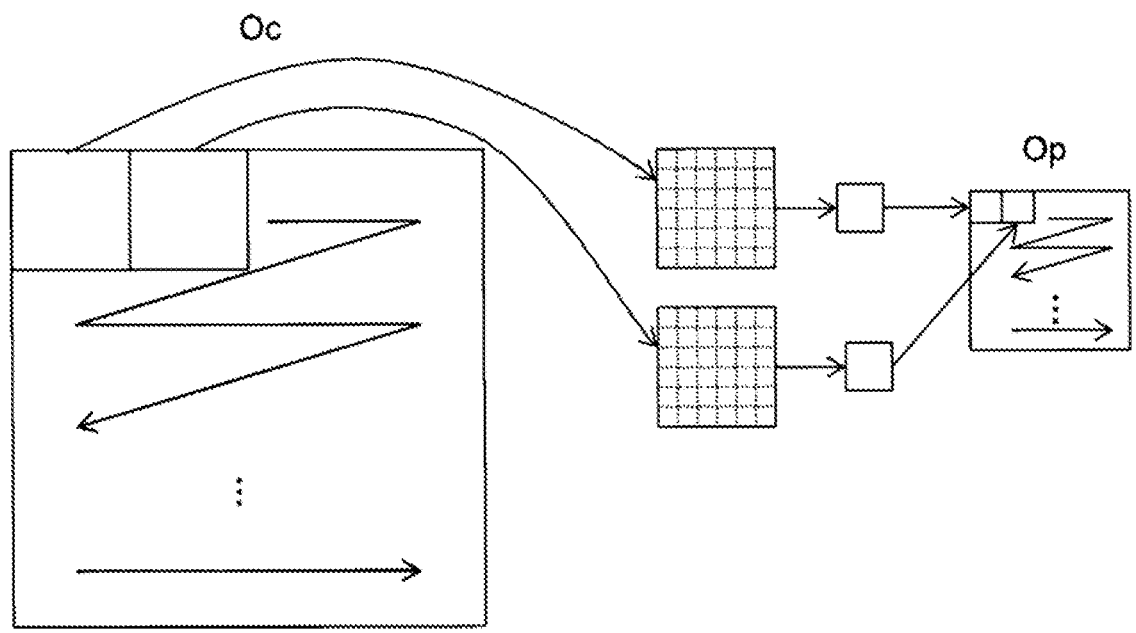
[Fig. 7A]
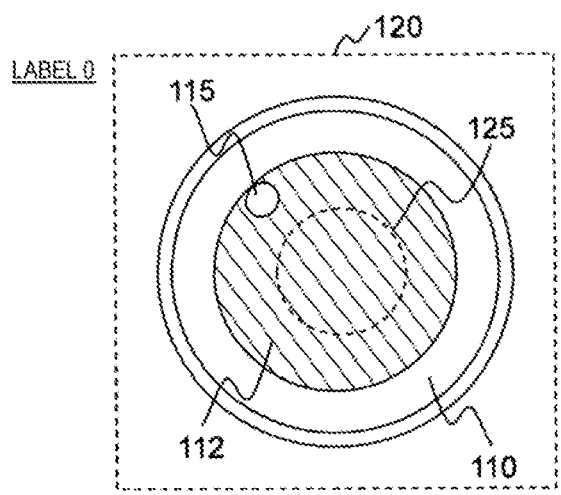

[Fig. 7B]
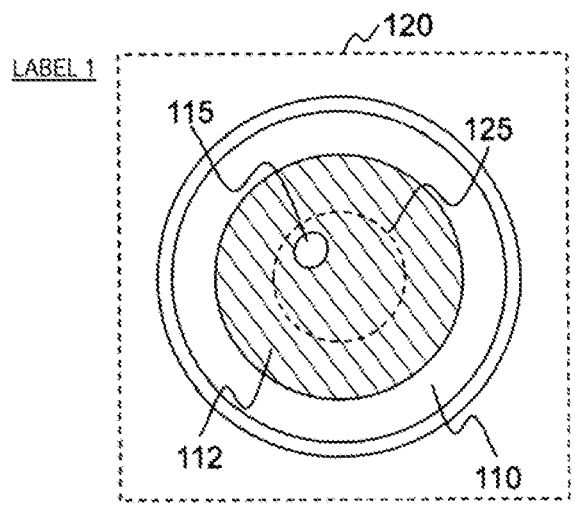
[Fig. 7C]
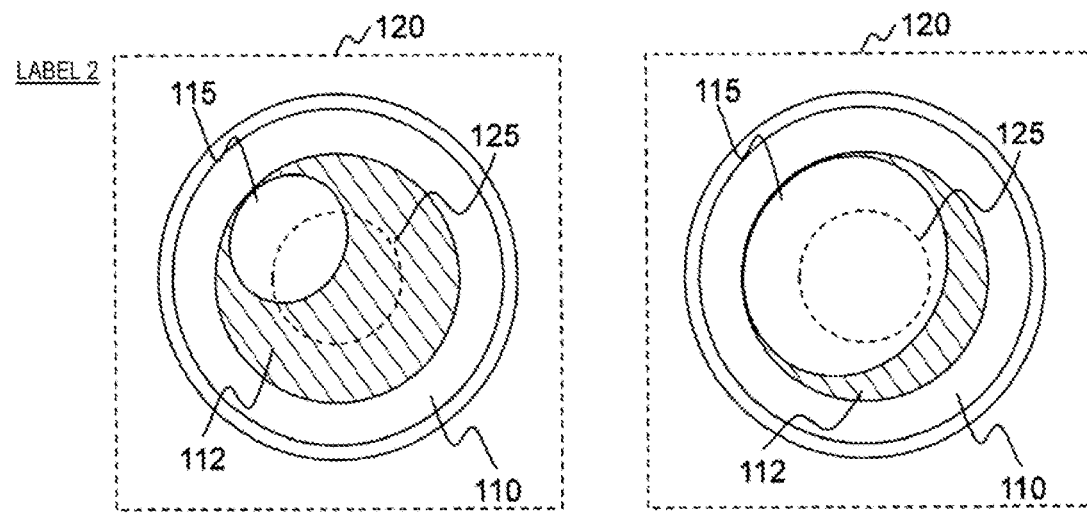

[Fig. 8]
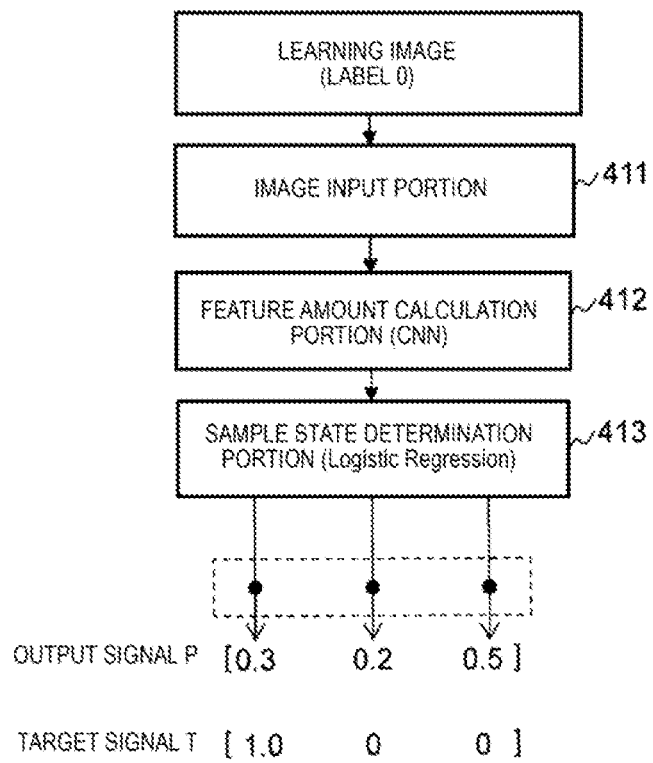
[Fig. 9]
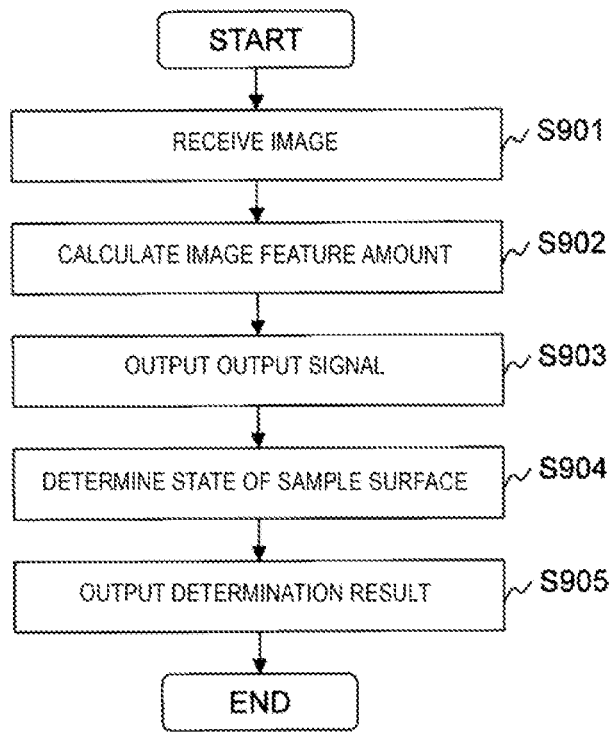

[Fig. 10]
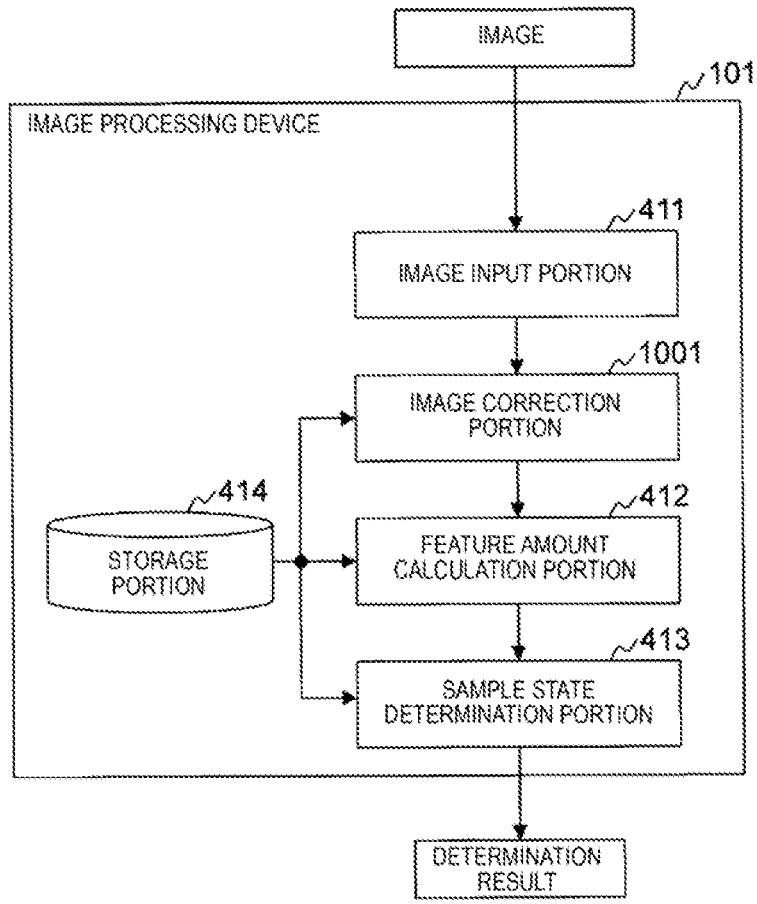
[Fig. 11]
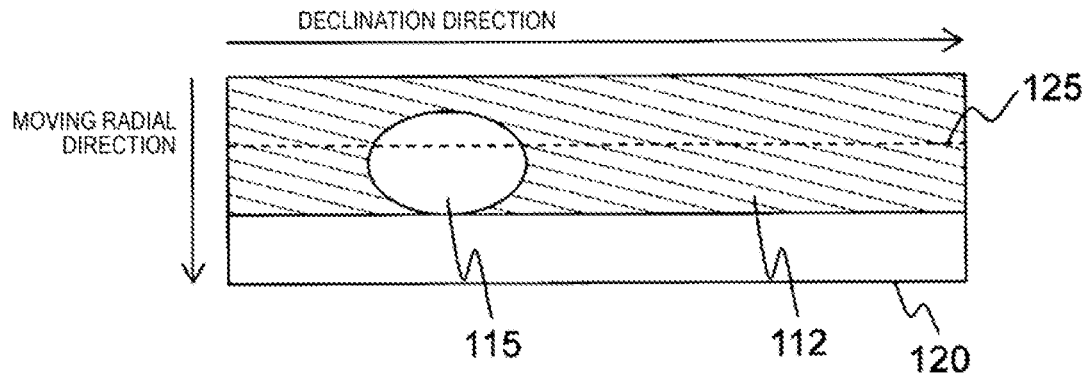

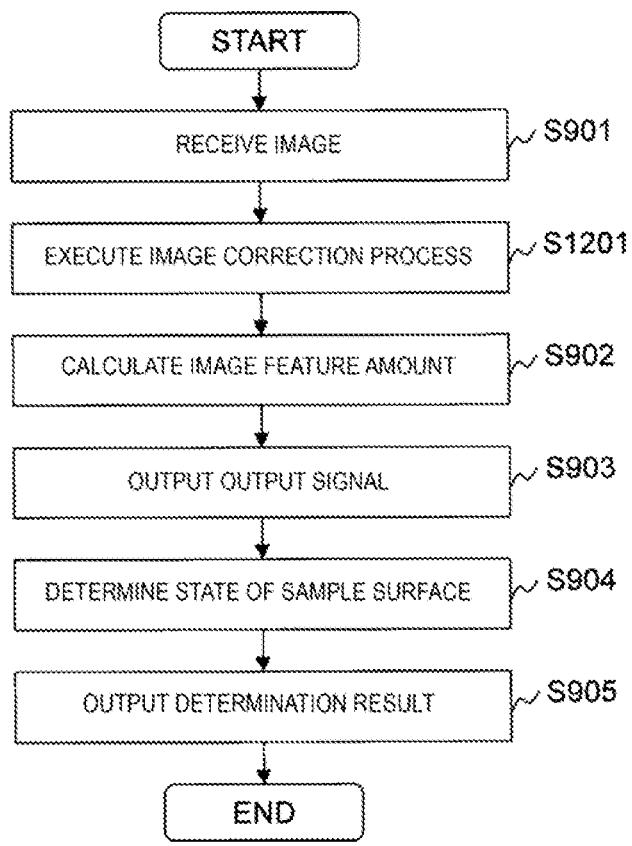
[Fig. 12]

[Fig. 13]
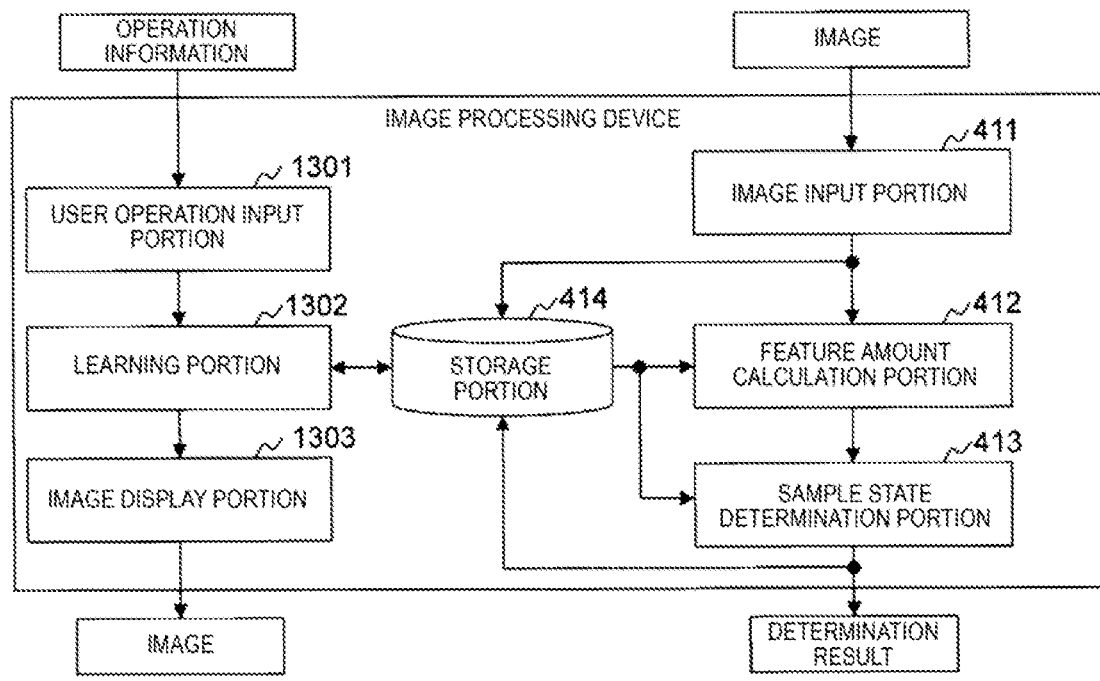

[Fig. 14]
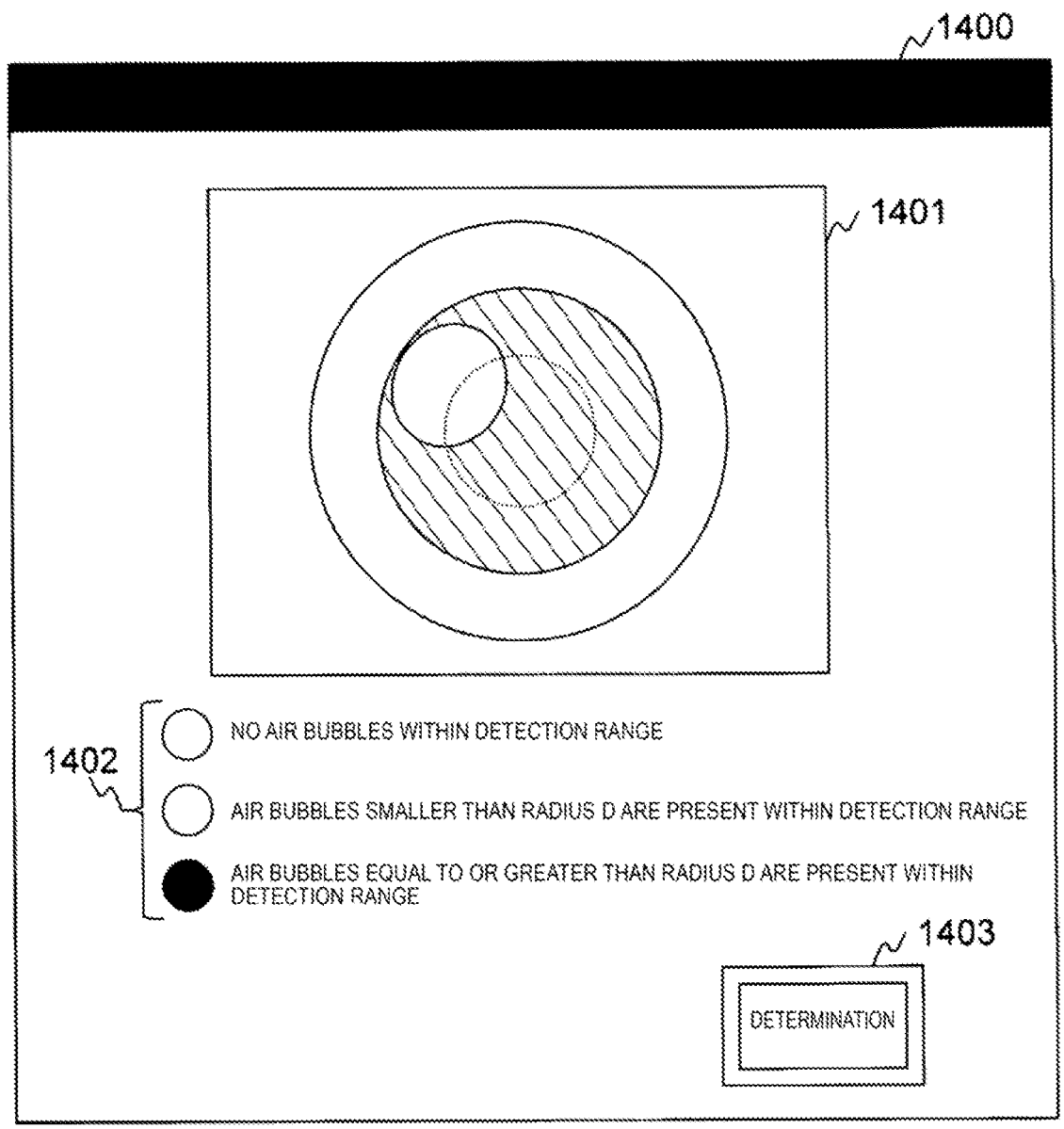

[Fig. 15]
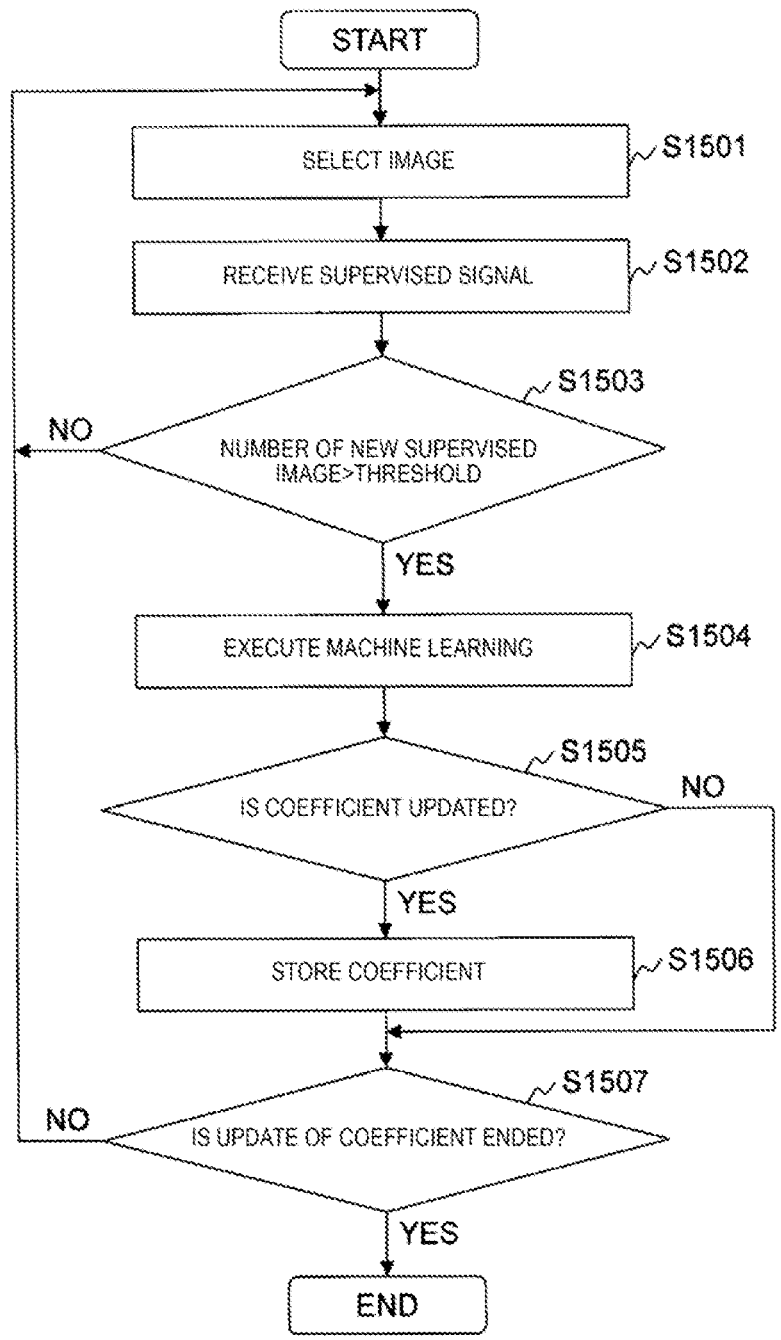

APPARATUS, METHOD FOR DETERMINING STATE OF SAMPLE, AND ANALYSIS SYSTEM

INCORPORATION BY REFERENCE

This application is based upon and claims the benefit of priority from Japanese Patent Application No. 2017-147629, filed Jul. 31, 2017, the entire contents of which are incorporated herein by reference.

TECHNICAL FIELD

The present invention relates to a technique for determining a state of a sample to be analyzed by an image process in an automatic analysis system configured with an immunoanalysis device or the like.

BACKGROUND ART

An analysis device such as an immunoanalysis device produces a reaction between a sample and a reagent and measures states of color development and light emission for analyzing components or the like of a sample such as blood or urine.

A sample to cause a reaction of the reagent is collected from a container that contains therein the sample using a dispensing probe or the like. Since a tip end of the dispensing probe is immersed in the sample and the sample is drawn in by suction, the sample adheres to the tip end and an outer wall of the dispensing probe.

In a case of a large amount of immersion of the dispensing probe, an amount of the sample adhering to the dispensing probe increases. This produces a problem of increasing an amount of the sample to be delivered in a case of collecting a new sample next time. To address the problem, therefore, an automatic analysis device having a liquid level detection function to reduce the delivery of the sample currently gains in popularity. Since the amount of immersion of the tip end of the dispensing probe can be controlled by detecting a liquid level, it is possible to reduce the delivery of the sample and draw in an appropriate amount of sample by suction.

However, in a case of presence of air bubbles on a sample surface, then the automatic analysis device falsely detects an air bubble surface as the liquid level, and performs a suction operation with the dispensing probe out of contact with the sample. Therefore, in the case of the presence of air bubbles on the sample surface, problems occur that it is impossible to draw in a sufficient amount of sample by suction and obtain an accurate analysis result. Owing to these, it is necessary to determine a state of the sample surface at a time of analysis.

There are known techniques described in Patent Documents 1 and 2 to address the problems. Patent Document 1 describes a method including capturing an image of a sample surface from an opening portion side of a container, and detecting air bubbles within the container by an image process. Furthermore, Patent Document 2 describes a method including capturing an image of an interior of a culture device and extracting an air bubble region within the culture device from a difference in color from a surrounding culture medium.

PRIOR ART DOCUMENT

Patent Documents

Patent Document 1: US Patent Application Publication No. 2013/0315486
Patent Document 2: JP-2016-510211-T

SUMMARY OF THE INVENTION

Problems to be Solved by the Invention

With the technique described in Patent Document 1, a distribution of air bubbles is obtained by calculating a histogram of an edge component per small region within the image for the image of the sample surface captured from the opening portion side of the container. Furthermore, with the technique described in Patent Document 1, a border of a container opening portion and center coordinates of the container opening portion are detected, and a part including a center of the container opening portion and near the center is set as an air bubble detection range.

However, the technique described in Patent Document 1 pays no attention to a size of air bubbles. Therefore, even if small air bubbles that do not affect analysis are detected, the sample is not drawn in by suction, resulting in a reduction in analysis efficiency. Moreover, in a case of presence of large air bubbles covering the air bubble detection range within the container, an edge near a border of the air bubbles is generated not inside but outside of the detection range; thus, the technique of detecting air bubbles using the edge component or the like is incapable of detecting air bubbles.

Furthermore, with the technique described in Patent Document 2, the air bubble region is extracted on the basis of the difference in color from the culture medium. However, an enormous amount of pattern images are possibly input to the automatic analysis device such as the immunoanalysis device depending on combinations of various factors such as a type and a color tone of a sample, a height of the liquid level, an intensity of illumination, a type of the container, presence/absence of liquid level vibration, presence/absence of a separating agent and beads, presence/absence of lipid, and reflections of printed letters of a test tube. It is, therefore, difficult to extract the air bubble region only on the basis of the difference in color.

An object of the present invention is to determine a state of a sample at a time of analysis without reductions in analysis accuracy and analysis efficiency.

Means for Solving the Problems

A typical example of the invention disclosed in the present application is as follows. That is, there is provided an apparatus for determining a state of a sample to be analyzed contained in a container, including: a computation device; and a storage device connected to the computation device, the computation device acquiring an image of the sample, analyzing a position and a size of an object to be detected with respect to a detection range set in the image using the image of the sample, and determining the state of the sample on the basis of a result of the analysis.

Advantages of the Invention

According to the present invention, it is possible to determine a state of a sample at a time of analysis without reductions in analysis accuracy and analysis efficiency by taking into account a position and a size of an object to be detected with respect to a detection range. Objects, configurations, and effects other than those described above will be readily apparent from the description of Examples given below.

BRIEF DESCRIPTION OF DRAWINGS

FIG. 1 is a view illustrating a configuration example of an automatic analysis system according to Example 1.

FIG. 2 is a view illustrating an example of a GUI for setting a threshold in an image processing device according to Example 1.

FIG. 3A is a view for explaining a relationship between a installation state of a container and a detection range with respect to an image acquisition device of Example 1.

FIG. 3B is a view for explaining the relationship between the installation state of the container and the detection range with respect to the image acquisition device of Example 1.

FIG. 4 is a view illustrating an example of a hardware configuration and a software configuration of the image processing device according to Example 1.

FIG. 5 is a view illustrating a concept of a convolution process executed by a feature amount calculation portion according to Example 1.

FIG. 6 is a view illustrating a concept of a pooling process executed by the feature amount calculation Portion according to Example 1.

FIG. 7A is a view illustrating an example of classification of a state of a sample surface according to Example 1.

FIG. 7B is a view illustrating an example of classification of a state of a sample surface according to Example 1.

FIG. 7C is a view illustrating an example of classification of a state of a sample surface according to Example 1.

FIG. 8 is a view illustrating an example of supervised machine learning of according to Example 1.

FIG. 9 is a view illustrating an example of a process of determining the state of the sample surface executed by the image processing device according to Example 1.

FIG. 10 is a view illustrating an example of a software configuration of an image processing device according to Example 2.

FIG. 11 is a view illustrating an example of an image correction process according to Example 2.

FIG. 12 is a view illustrating an example of a process of determining of a state of a sample surface executed by the image processing device according to Example 2.

FIG. 13 is a view illustrating an example of a software configuration of an image processing device according to Example 3.

FIG. 14 is a view illustrating an example of a GUI displayed by the image processing device according to Example 3.

FIG. 15 is a flowchart for explaining an example of a process executed by a learning portion according to Example 3.

MODES FOR CARRYING OUT THE INVENTION

Modes for carrying out the present invention will be described hereinafter with reference to the accompanying drawings. In the accompanying drawings, functionally same elements are often denoted by the same reference signs. While the accompanying drawings illustrate specific modes for carrying out the invention according to the principle of the present invention, these are given to help understand the present invention and are not intended to be used to interpret the present invention in a limited fashion.

While the present modes for carrying out the invention are described sufficiently in detail for a person having ordinary skill in the art to carry out the present invention, it is necessary to understand that other implementations and forms are also applicable, and that configurations and structures can be changed and various elements can be replaced without departure of the scope and spirit of technical concept of the present invention. Therefore, the following description is not to be interpreted while being limited to the modes for carrying out the invention.

Moreover, as described later, the modes for carrying out the present invention may be implemented as software that runs on a general-purpose computer or may be implemented as dedicated hardware or a combination of software and hardware.

Describing each process with a functional portion assumed as a subject (operation subject) hereinafter indicates that a computation device executes a program that realizes the functional portion. Furthermore, part of or entirety of the program that realizes each functional portion may be realized using dedicated hardware or may be modularized. Various programs may be installed into an image processing device by a program distribution server or a storage medium.

Example 1

In Example 1, a device that executes an image process of determining a state of a sample surface from a position and a size of an object to be detected (such as air bubbles) with respect to a detection range set in an image of the sample surface obtained by imaging a sample surface in a container on the basis of the image, and a system including the device will be described.

FIG. 1 is a view illustrating a configuration example of an automatic analysis system according to Example 1.

The automatic analysis system includes an image processing device 101, a lighting device 102, an image acquisition device 103, a sample acquisition device 104, a sample analysis device 106, and an output device 107, and also includes a device that installs a container 110 in which a sample 111 is contained.

The sample 111 is a sample to be analyzed such as blood or urine. A sample surface 112 is a liquid level of the sample 111. The container 110 is a container such as a test tube for containing therein the sample 111.

The sample acquisition device 104 is a suction device having a dispensing probe or the like for drawing in the sample 111 by suction. The sample acquisition device 104 controls a dispensing probe 105 to acquire the sample 111 contained in the container 110.

The lighting device 102 is a device such as an LED that emits light toward the sample surface 112 from an opening portion side of the container 110. The image acquisition device 103 is a device such as a camera that acquires an image of the sample surface 112 from the opening portion side.

The image acquisition device 103 according to Example 1 acquires the image of the sample surface 112 and outputs an image in a range indicated by an image acquisition range 120 to the image processing device 101. The image illustrated in FIG. 1 is an image of the sample surface 112 captured from the opening portion side of the container 110.

An object to be detected 115 is an object, a substance, or the like involved in control over acquisition of the sample 111. In Example 1, air bubbles are regarded as the object to be detected 115. Furthermore, a detection range 125 is a range which is set in the image and in which the object to be detected 115 is detected. Since the detection range 125 is the range set with respect to the image acquisition range 120, the detection range 125 does not depend on a position and a size of the container 110 in the image.

The image processing device 101 determines a state of the sample surface 112 by analyzing the image input from the image acquisition device 103.

An outline of processes performed by the automatic analysis system will now be described.

First, the container 110 in which the sample 111 is contained is installed at a predetermined position with respect to the image acquisition device 103. In the example illustrated in FIG. 1, the container 110 is disposed immediately under the image acquisition device 103.

The lighting device 102 adjusts an angle and an intensity of light so that the sample surface 112 has an appropriate brightness. The image acquisition device 103 acquires the image of the sample surface 112 and outputs the acquired image to the image processing device 101. At this time, it is assumed that the sample acquisition device 104 has moved to a position at which the sample acquisition device 104 does not disturb the acquisition of the image by the image acquisition device 103.

In a case of inputting the image to the image processing device 101, the image processing device 101 determines the state of the sample surface 112 on the basis of a position and a size of the object to be detected 115 with respect to the detection range 125 in the image. The image processing device 101 outputs a determination result to the sample acquisition device 104. In addition, the image processing device 101 outputs data such as the determination result to the output device 107 as needed.

While the image processing device 101 is described as an independent computing machine in Example 1, the image processing device 101 may be implemented as a function in an automatic analysis device such as an immunoanalysis device.

In a case of receiving the determination result from the image processing device 101, the sample acquisition device 104 determines a content of control on the basis of the determination result. Specifically, the sample acquisition device 104 determines whether to acquire the sample 111 from the container 110. In a case of determining to acquire the sample 111, the sample acquisition device 104 moves down the dispensing probe 105 toward the sample 111. In a case in which the dispensing probe 105 comes in contact with the sample surface 112, the sample acquisition device 104 detects the liquid level by a liquid level detection function and stops moving down the dispensing probe 105. The sample acquisition device 104 causes the dispensing probe 105 to perform an operation such as suction of the sample 111 in a state in which a tip end of the dispensing probe 105 is slightly immersed in the sample surface 112. Through these processes, the sample acquisition device 104 acquires the sample 111 from the container 110.

The sample analysis device 106 is a device that analyzes the sample 111 acquired by the sample acquisition device 104 and is, for example, an immunoanalysis device. The sample analysis device 106 outputs an analysis result to the output device 107.

The output device 107 is a device that presents the analysis result to a user and is, for example, a display, a printer, and a communication device. In addition, the output device 107 presents information output from the image processing device 101 to the user.

With the conventional techniques described in Patent Document 1 and the like, in a case of determining whether an object to be detected is present, the device calculates the border of the container or the center coordinates of the opening portion of the container on the basis of the Hough transform or the like. In general, a process of calculating the center coordinates of the opening portion of the container causes increases in processing cost and processing time. To reduce the processing cost and the processing time, therefore, it is desirable to adopt a technique for determining the position and the size of the object to be detected without calculating the center coordinates of the opening portion of the container.

The image processing device 101 according to Example 1 determines the state of the sample surface 112 on the basis of a relative position relationship between the detection range 125 that does not depend on the position and the size of the container 110 in the image and the object to be detected 115 and a relative size relationship between a size of the detection range 125 and the size of the object to be detected 115.

In Example 1, the detection range 125 and a threshold of the size of the object to be detected 115 that does not affect analysis is set as information for determining the state of the sample surface 112.

Since the size of the object to be detected 115 is one of indexes for determining whether the size thereof affects analysis, it is necessary to take into account the size of the object to be detected 115. It is conceivable, for example, to set a maximum radius of the object to be detected 115 that does not affect analysis as the threshold.

It is noted that the user may set the threshold using a GUI. FIG. 2 is a view illustrating an example of the GUI for setting the threshold in the image processing device 101 according to Example 1.

A GUI 200 includes a threshold input field 201 and a determination button 202. The threshold input field 201 is a field to which a value set as the threshold is input. The determination button 202 is an operation button for setting the value input to the threshold input field 201 in the image processing device 101.

The user sets the value indicating the maximum radius of air bubbles or the like in the threshold input field 201 and depresses the determination button 202. The threshold is thereby set in the image processing device 101.

It is noted that the GUI 200 illustrated in FIG. 2 is given as an example and that input fields for setting the detection range 125 and the image acquisition range 120 may be provided.

Furthermore, choices such as processing time and a processing load may be displayed as an alternative to direct input of a numeric value. In this alternative, a threshold in response to each choice is set in the image processing device 101.

FIGS. 3A and 3B are views for explaining a relationship between an installation state of the container 110 and the detection range 125 with respect to the image acquisition device 103 according to Example 1.

The image acquisition range 120 indicates a range of the image to be output to the image processing device 101. In Example 1, the image acquisition range 120 is set larger than the container 110 in light of a deviation or the like of the installation position of the container 110. The image in the image acquisition range 120 includes the container 110, the sample surface 112, and the object to be detected 115. The detection range 125 is set with respect to the image acquisition range 120. It is noted that the image acquisition range 120 is not necessarily a range encompassing the container 110 and can be arbitrarily set.

To detect the large object to be detected 115 encompassing the detection range 125, the image acquisition range 120 is desirably set larger than a distribution range of the object to be detected 115. A region of (E×E) pixels with a center of the image assumed as an origin is set to the image acquisition range 120 in Example 1. It is noted that a value larger than a diameter of the container 110 is set to E indicating each of horizontal and vertical sizes.

The detection range 125 is a range with a point at which the tip end of the dispensing probe 105 comes in contact with the sample surface 112, and the range does not depend on the center coordinates of the container 110. It is noted that the detection range 125 is set as a circular range of pixels at a radius R.

An installation angle and an installation position of the container 110 with respect to the image acquisition device 103 often vary. To draw in the sample 111 of an amount suited for analysis by suction in response to such a variation, it is important to determine whether the object to be detected 115 is present around the tip end of the dispensing probe 105 that comes in contact with the sample surface 112. In Example 1, therefore, it is determined whether the object to be detected 115 is present on the basis of the detection range 125.

Since a center of the opening portion of the container 110 is not used as a basis for determination in a determination method in Example 1, it is unnecessary to calculate the center of the opening portion of the container 110. It is, therefore, possible to reduce the processing time and the processing load, compared with the conventional techniques.

FIGS. 3A and 3B illustrate two detection ranges 125 and 126. The detection range 125 is the detection range adopted in the present invention and is the range of pixels at the radius R with the point at which the tip end of the dispensing probe 105 comes in contact with the sample surface 112 assumed as the origin. The detection range 126 is a detection range adopted in the conventional techniques and is a range of pixels at the radius R with the center of the opening portion of the container 110 assumed as an origin.

FIG. 3A illustrates a state in which the installation angle of the container 110 with respect to the image acquisition device 103 has a variation. At this time, a deviation is generated between the center of the opening portion of the container 110 and a center of the image acquisition range 120. Therefore, a deviation is also generated between the detection ranges 125 and 126 as illustrated in FIG. 3A.

As illustrated in FIG. 3A, the object to be detected 115 is included in the detection range 125 but is not included in the detection range 126. A part in which the tip end of the dispensing probe 105 comes in contact with the sample surface 112 at a time of acquiring the sample 111 is inside of the detection range 125. It is, therefore, desirable to determine that the state illustrated in FIG. 3A is a state in which the object to be detected 115 that affects analysis is present.

In a case of executing a determination process based on the detection range 125, it is determined that the state illustrated in FIG. 3A is the state in which the object to be detected 115 is present. On the other hand, in a case of executing a determination process based on the detection range 126, it is determined that the state illustrated in FIG. 3A is a state in which the object to be detected 115 is not present. Therefore, the object to be detected 115 can be accurately detected in the determination process based on the detection range 125, while detection accuracy does not improve due to the deviation described above in the determination process based on the detection range 126.

FIG. 3B illustrates a state in which the installation position of the container 110 with respect to the image acquisition device 103 has a variation. At this time, a deviation is generated between the center of the opening portion of the container 110 and the center of the image acquisition range 120. Therefore, a deviation is also generated between the detection ranges 125 and 126 as illustrated in FIG. 3B.

As illustrated in FIG. 3B, the object to be detected 115 is not included in the detection range 125 but is included in the detection range 126. The part in which the tip end of the dispensing probe 105 comes in contact with the sample surface 112 at the time of acquiring the sample 111 is inside of the detection range 125. It is, therefore, desirable to determine that the state illustrated in FIG. 3B is a state in which the object to be detected 115 that affects analysis is not present.

In the case of executing a determination process based on the detection range 125, it is determined that the state illustrated in FIG. 3B is the state in which the object to be detected 115 is not present. On the other hand, in a case of executing a determination process based on the detection range 126, it is determined that the state illustrated in FIG. 3B is the state in which the object to be detected 115 is present. Therefore, it is possible to avoid excessive detection of the object to be detected 115 in the determination process based on the detection range 125, while excessive detection of the object to be detected 115 occurs in the determination process based on the detection range 126.

As described above, in Example 1, using the detection range 125 with the point at which the tip end of the dispensing probe 105 comes in contact with the sample surface 112 assumed as the center makes it possible to highly accurately determine whether the state is the state that the object to be detected 115 affects analysis even in cases of occurrence of changes in an inclination and the installation position of the container 110. Furthermore, in Example 1, since it is unnecessary to calculate the center coordinates of the opening portion of the container 110, it is possible to reduce the processing cost and the processing time, compared with the conventional techniques.

The image processing device 101 according to Example 1 will next be described in detail. FIG. 4 is a view illustrating an example of a hardware configuration and a software configuration of the image processing device 101 according to Example 1.

The image processing device 101 has a computation device 401, a storage device 402, an input device 403, and an output device 404.

The computation device 401 is a device that executes programs stored in the storage device 402 and is, for example, a CPU or an FPGA. The computation device 401 operates as a functional portion (module) that realizes a predetermined function by executing a process in accordance with each program. In the description hereinafter, describing a process with a functional portion assumed as a subject indicates that the computation device 401 executes the program that realizes the functional portion.

As for each of functional portions owned by the image processing device 101, a plurality of functional portions may be integrated into one functional portion or one functional portion may be divided into a plurality of functional portions.

The storage device 402 is a device that stores the programs executed by the computation device 401 and information for using the programs, and is, for example, a memory, an HDD (Hard Disk Drive), an SSD (Solid State Drive), a RAM (Random Access Memory), or a ROM (Read Only Memory). It is noted that the storage device 402 includes a work area that is temporarily used by the programs. The programs and the information stored in the storage device 402 will be described later.

The input device 403 is a device that inputs data to the image processing device 101 and includes, for example, a network interface, a keyboard, a mouse, and a touch panel. In Example 1, the image acquired by the image acquisition device 103 is input to the image processing device 101 via the input device 403.

It is noted that the input image may be a still image in a BPM, PNC, JPEG format, or the like, or frame images extracted from a moving image in an MPEG, H.264 format, or the like at fixed intervals.

The output device 404 is a device used for the image processing device 101 to output data and includes, for example, a network interface, a display, or a printer. In Example 1, a determination result is output to the sample acquisition device 104 via the output device 404.

The programs and the information stored in the storage device 402 will now be described.

The storage device 402 stores the programs that realize an image input portion 411, a feature amount calculation portion 412, a sample state determination portion 413, and a storage portion 414.

The image input portion 411 receives the image input via the input device 403 and outputs the image to the feature amount calculation portion 412.

The feature amount calculation portion 412 calculates an image feature amount from the image and outputs the image feature amount to the sample state determination portion 413.

The sample state determination portion 413 analyzes the position and the size of the object to be detected with respect to the detection range in the image on the basis of the image feature amount, and determines the state of the sample surface 112 on the basis of an analysis result.

The storage portion 414 stores information about a determination model for determining the state of the sample surface 112. Specifically, the storage portion 414 stores coefficients used by the feature amount calculation portion 412 and the sample state determination portion 413.

Operations performed by the feature amount calculation portion 412 and the sample state determination portion 413 will next be described in detail.

First, operations performed by the feature amount calculation portion 412 will be described. The feature amount calculation portion 412 reads the coefficients from the storage portion 414 and calculates the image feature amount using the coefficients and the image. The coefficients used by the feature amount calculation portion 412 are derived on the basis of machine learning or the like in advance and stored in the storage portion 414. A method for deriving the coefficients will be described later.

In Example 1, a calculation method using a convolutional neural network (CNN) will be described as an example of a method for calculating the image feature amount. The CNN is configured from three types of processes, that is, a convolution process, a pooling process, and an activation process.

FIG. 5 is a view illustrating a concept of the convolution process executed by the feature amount calculation portion 412 according to Example 1.

In the convolution process, the feature amount calculation Portion 412 calculates a feature amount using Equation (1). As indicated by arrows, the feature amount calculation portion 412 executes computation of Equation (1) on the image in a direction from upper left to lower right of the image.

[Equation 1]

$$Oc(d, y, x) = \sum_{ch}\sum_{fy}\sum_{fx} (Ic(ch, y+fy, x+fx) \times Wc(d, ch, fy, fx)) + Bc(d) \quad (1)$$

In Equation (1), Ic denotes input data, Wc denotes a multiplication coefficient, Bc denotes an addition coefficient, and Oc denotes output data. In addition, ch denotes a channel, y and fy denote vertical positions, x and fx denote horizontal positions, and d denotes a feature amount number.

The input data Ic is data in a dimension having the channel ch, the vertical position y, and the horizontal position x. The multiplication coefficient Wc is a coefficient in a dimension having the feature amount number d, the channel ch, the vertical position fy, and the horizontal position fx. The addition coefficient Bc is a coefficient in a dimension having the feature amount number d. The output data 303 is data in a dimension having the feature amount number d, the vertical position y, and the horizontal position x.

The multiplication coefficient Wc and the addition coefficient Bc are the coefficients for calculating the image feature amount, and stored in the storage portion 414.

FIG. 6 is a view illustrating a concept of the pooling process executed by the feature amount calculation portion 412 according to Example 1.

In the pooling process, the feature amount calculation portion 412 extracts partial regions at a fixed step size from the output data Oc from upper left to lower right, calculates representative values from the partial regions, and outputs output data Op. As the representative values, maximum values or average values, for example, are used.

In the activation process, the feature amount calculation portion 412 executes a computation process using a nonlinear function such as a tan h function expressed in Equation (2) or an ReLU function expressed in Equation (3) on the output data Op. Here, the output data Op is input to x.

[Equation 2]

$$\tanh(x) = \frac{e^x - e^{-x}}{e^x + e^{-x}} \quad (2)$$

[Equation 3]

$$ReLu(x) = \max(0, x) \quad (3)$$

In the CNN, the feature amount calculation portion 412 calculates the image feature amount by repeatedly executing the convolution process, the pooling process, and the activation Process. In a case in which the number of times of repetition reaches a specified number of times, the feature amount calculation portion 412 outputs a value calculated by the final activation process as the image feature amount.

Operations performed by the sample state determination portion 413 will next be described. The sample state determination portion 413 analyzes the position and the size of the object to be detected 115 with respect to the detection range 125 in the image using the image feature amount calculated by the feature amount calculation portion 412 and the coefficients stored in the storage portion 414, and determines the state of the sample surface 112 on the basis of the analysis result. Specifically, the sample state determination portion 413 performs classification to determine which of preset states the input image belongs to. The coefficients used by the sample state determination portion 413 are derived on the basis of machine learning or the like in advance and stored in the storage portion 414. A method for deriving the coefficients will be described later.

Classification of the state of the sample surface 112 will first be described. FIGS. 7A, 7B, and 7C are views illustrating examples of classification of the state of the sample surface 112 according to Example 1.

States are roughly classified into a state in which the object to be detected 115 that affects analysis is present in the detection range 125 and a state in which the object to be detected 115 that affects analysis is not present in the detection range 125. Images belonging to the two states have various patterns depending on the device, the sample, an analysis performance, an analysis purpose, and the like. In Example 1, the states of the sample surface 112 are classified into three states depending on a relationship of the position and the size of the object to be detected 115 with respect to the detection range 125 in the image while state identification accuracy is taken into account. Labels 0, 1, and 2 are allocated to the respective states.

FIG. 7A illustrates an example of an image with the label 0. In the image, the object to be detected 115 is not present in the detection range 125.

FIG. 7B illustrates an example of an image with the label 1. In the image, the object to be detected 115 having a radius d1 smaller than a threshold D is present in the detection range 125. In other words, the image is in the state in which the object to be detected 115 at a size that does not affect analysis is present in the detection range 125.

FIG. 7C illustrates an example of images with the label 2. In the left image, the object to be detected 115 having a radius d2 equal to or greater than the threshold D is present in the detection range 125. In the right image, the object to be detected 115 having a radius d3 equal to or greater than the threshold D is present to cover the detection range 125. In other words, the images are each in the state in which the object to be detected 115 at a size that affects analysis is present in the detection range 125.

In Example 1, the states of the sample surface 112 to which the labels 0 and 1 are allocated belong to the state in which the object to be detected 115 that affects analysis is not present in the detection range 125, while the sample surface 112 to which the label 2 is allocated belongs to the state in which the object to be detected 115 that affects analysis is present in the detection range 125. In this way, the state of the sample surface 112 to be classified is specified in response to the position and the size of the object to be detected 115 with respect to the detection range 125 in the image. In Example 1, a label (supervised signal) corresponding to the state of the sample surface 112 is allocated to a learning image.

In Example 1, in a case in which the state of the image is classified into the state to which the label 0 or label 1 is allocated, the sample acquisition device 104 is controlled to acquire the sample 111. In a case in which the image is classified into the state to which the label 2 is allocated, the sample acquisition device 104 is controlled not to acquire the sample.

A determination method using logistic regression will next be described as an example of the method for determining the state of the sample surface 112. Equation (4) is an equation used in the logistic regression. In addition, Equation (5) indicates a method for calculating a softmax function in Equation (4).

[Equation 4]

$$P(c) = \text{softmax}\left(\sum_d \sum_y \sum_x (F(d, y, x) \times Wr(c, d, y, x)) + Br(c)\right) \quad (4)$$

[Equation 5]

$$\text{softmax}(x_c) = \frac{e^{x_c}}{\sum_j e^{x_j}} \quad (5)$$

In Equations (4) and (5), P(c) denotes an output value, F denotes an image feature amount, Wr denotes a multiplication coefficient, and Br denotes an addition coefficient. In addition, y denotes a vertical position, x denotes a horizontal position, d denotes a feature amount number, and c denotes an output unit number. In Example 1, the output unit number corresponds to the label 0, the label 1, or the label 2. P(c) is a value that denotes a likelihood of the label corresponding to the output unit.

The image feature amount F is data in a dimension having the feature amount number d, the vertical position y, and the horizontal position x. The multiplication coefficient Wr is a coefficient in a dimension having the output unit number c, the feature amount number d, the vertical position y, and the horizontal position x. The addition coefficient Br is a coefficient in a dimension having the output unit number c. Furthermore, the output value P(c) is a value in a dimension having the output unit number c.

The multiplication coefficient Wr and the addition coefficient Br are the coefficients for calculating the determination result, and stored in the storage portion 414.

The sample state determination portion 413 outputs output values P(c) indicating the likelihoods of the three labels as an output signal P. It is noted that the likelihood of each label is the value calculated on the basis of Equation (4).

The sample state determination portion 413 identifies the label allocated to the state with which the state of the sample surface 112 coincides on the basis of the output signal P. In other words, the sample state determination portion 413 analyzes the position and the size of the object to be detected 115 with respect to the detection range 125. Furthermore, the sample state determination portion 413 outputs the determination result on the basis of the state to which the identified label is allocated. The sample state determination portion 413 outputs, for example, one label as the determination result. Alternatively, the sample state determination portion 413 may determine whether the sample surface 112 is in the state in which the sample 111 can be acquired on the basis of the label.

The method for deriving coefficients stored in the storage portion 414 will next be described. The method for deriving coefficients based on supervised learning that is a type of machine learning will be described by way of example.

FIG. 8 is a view illustrating an example of supervised machine learning according to Example 1.

In the supervised learning, a device having a learning portion receives input learning data (learning image) to which the supervised signal is allocated in advance, causes the feature amount calculation portion 412 and the sample state determination section 413 to execute the processes, and performs learning of a determination tool or the like so that the output signal coincides with a target signal corresponding to the supervised signal (label). In Example 1, each of the coefficients in Equations (1) and (4) is optimized on the basis of the supervised learning. It is thereby possible to set the coefficients for obtaining a highly accurate determination result with respect to the input image. It is noted that the device having the learning portion may include configurations equivalent to those of the feature amount calculation portion 412 and the sample state determination portion 413.

To classify the state into any of the three states illustrated in FIGS. 7A, 7B, and 7C, it is necessary to allocate the supervised signal (label) to the learning image in response to the position and the size of the object to be detected 115 with respect to the detection range 125 in advance.

It is noted that an initial value of each coefficient before start of a learning process may be arbitrarily set using a random number or the like or set on the basis of a previous learning process.

Specifically, the learning portion derives each of the coefficients stored in the storage portion 414 in accordance with the following process.

(Step S1) The learning portion receives the input learning image to which the supervised signal is allocated, and inputs the learning image to the feature amount calculation portion 412 and the sample state determination portion 413, thereby acquiring an output signal. The learning portion defines a target function of the output signal and the target signal illustrated in Equation (6). Equation (6) expresses a negative log likelihood.

[Equation 6]

$$nll = \sum_c (T(c) \times \log(P(c)) + (1 - T(c) \times \log(1 - P(c)))) \qquad (6)$$

In Equation (6), T(c) denotes element of the target signal. The target signal T in Example 1 is a sequence of T(c) representing the target values of the three labels. Among the values of the elements of the target signal T, the value of only the element corresponding to the label is "1.0" and those of the other elements are all "0.0." Since the learning image to which the label 0 is allocated is input in FIG. 8, only T(c) corresponding to the label 0 takes on "1.0" and T(c) corresponding to each of the other labels takes on "0.0" in the target signal T.

It is noted that the learning portion may hold functions identical to the feature amount calculation portion 412 and the sample state determination portion 413.

(Step S2) The learning portion updates each of the coefficients Wc, Bc, Wr, and Br by obtaining a coefficient for which the value of the target function is a minimal value by use of the gradient descent method. Specifically, the learning portion updates each of the coefficients in accordance with Equation (7).

[Equation 7]

$$w_{i+1} = w_i - \eta \frac{\partial nll}{\partial w_i} \qquad (7)$$

In Equation 7, $w_i$ denotes the coefficient corresponding to any of the coefficients Wc and Bc used in the CNN and the coefficients Wr and Br used in the logistic regression. In addition, i denotes the number of times of update. Furthermore, η denotes a learning rate that is a parameter for fixing an update width. A second term of Equation (7) is partial derivative of the coefficient $w_i$.

The learning portion derives each of the coefficients Wc, Bc, Wr, and Br for which the target function is minimal by repeatedly executing a computation process based on Equation (7). In Example 1, the coefficients derived by the above process are stored in the storage portion 414 in advance.

A process executed by the image processing device 101 according to Example 1 at a time of analyzing the sample 111 will be described in light of the principle, the features, and the processes described so far. FIG. 9 is a view illustrating an example of a process of determining the state of the surface of the sample 111 executed by the image processing device 101 according to Example 1.

The image input portion 411 of the image processing device 101 receives the image input from the image acquisition device 103 (Step S901).

The feature amount calculation portion 412 of the image processing device 101 reads the coefficients Wc and Bc from the storage portion 414, and calculates the image feature amount using the image and the coefficients (Step S902).

The sample state determination portion 413 of the image processing device 101 reads the coefficients Wr and Br from the storage portion 414, and outputs the output signal using the image feature amount and the coefficients (Step S903). Furthermore, the sample state determination section 413 determines the state of the sample surface 112 on the basis of the output signal (Step S904).

The sample state determination portion 413 of the image processing device 101 outputs the determination result (Step S905). The sample state determination portion 413 may output the determination result as it is or may convert a data format and a content of the determination result in response to an output destination. In a case, for example, in which the output destination is the display, the sample state determination portion 413 converts the determination result into data such as a character string or an image.

While control is exercised in such a manner that the sample 111 is not acquired in the case in which the state of the sample surface 112 is the state to which the label 2 is allocated in Example 1, control is not limited to this control. For example, the sample acquisition device 104 may have a device or a function that removes the object to be detected 115, and remove the object to be detected 115 and then acquire the sample 111 using the device or the function in a case in which the determination result indicating the label 2 is input. Examples of the device that removes the object to be detected 115 include a removal device such as a nozzle that delivers air and a removal device that emits an ultrasound wave.

While the method for calculating the image feature amount based on the CNN has been described as the method for calculating the image feature amount, the other feature amount calculation method such as circle detection by HOG (histograms of oriented gradients) and the Hough transform may be used.

While the determination method using the logistic regression has been described as the method for determining the state of the sample surface 112, a determination method using SVM (support vector machine), linear regression, or the like may be used.

While the label is allocated to the state in response to the position and the size of the object to be detected 115 with respect to the detection range 125 in the image in the case of deriving the coefficients on the basis of the machine learning, label allocation is not limited to this allocation. For example, a label for classifying the position of the object to be detected 115 with respect to the detection range 125 in the image and a label for classifying the size of the object to be detected 115 with respect to the detection range 125 in the image may be prepared. In this case, the sample state determination portion 413 has determination tools for determining different types of labels. Furthermore, the coefficients stored in the storage portion 414 are calculated by executing the machine learning for each label. The sample state determination portion 413 can obtain a final determination result by combining determination results of the two determination tools.

Moreover, a plurality of thresholds may be defined for the position or the size of the object to be detected 115 with respect to the detection range 125 in the image, and the types or number of labels may be increased. Furthermore, the number of labels may be reduced by handling the labels 0, 1, and the like as the same label.

While the determination result of the image processing device 101 is used in the control over the sample acquisition device 104 in Example 1, usage of the determination result is not limited to this example. The determination result of the image processing device 101 can be used as information for determining contents of various types of control associated with sample analysis. Moreover, the image processing device 101 is applicable to a system other than the automatic analysis system illustrated in FIG. 1.

As described so far, according to Example 1, the image processing device 101 can highly accurately determine the state of the sample surface 112 on the basis of the position and the size of the object to be detected 115 with respect to the detection range 125 in the image. Since this makes it possible to efficiently and accurately acquire the sample 111 to be analyzed from the container 110, it is possible to accurately analyze the sample 111 without reducing inspection efficiency.

Example 2

In Example 2, the image processing device 101 corrects the image input from the image acquisition device 103 and executes similar processes to those in Example 1 using the corrected image. Example 2 will be described hereinafter while mainly referring to differences from Example 1.

A system configuration according to Example 2 is identical to that according to Example 1. A hardware configuration of the image processing device 101 according to Example 2 is identical to that of the image processing device 101 according to Example 1. A software configuration of the image processing device 101 according to Example 2 partially differs from that according to Example 1. FIG. 10 is a view illustrating an example of the software configuration of the image processing device 101 according to Example 2.

Example 2 differs from Example 1 in that a program that realizes an image correction portion 1001 is stored in the storage device 402. Example 2 also differs from Example 1 in that parameters used by the image correction portion 1001 are stored in the storage portion 414.

It is noted that the image input portion 411, the feature amount calculation portion 412, and the sample state determination portion 413 are identical to those according to Example 1.

In a case of receiving an image from the image input portion 411, the image correction portion 1001 reads parameters from the storage portion 414 and executes an image correction process. Examples of the image correction process include coordinate transform and pixel value normalization.

FIG. 11 is a view illustrating an example of the image correction process according to Example 2.

FIG. 11 illustrates a result in a case of performing polar coordinate transform on the left image of FIG. 7C.

Since the detection range 125 is circular, it is necessary to determine whether the object to be detected 115 is included in the detection range 125 from a vertical position and a horizontal position in rectangular coordinates. On the other hand, in a case of executing the polar coordinate transform, then the detection range 125 is expressed in a rectangular form, and it is possible to determine whether the object to be detected 115 is included in the detection range 125 only from the vertical position.

Relationships of Equations (8) and (9) are held between a pixel position (x, y) in the rectangular coordinates and a pixel position (t, r) in polar coordinates.

[Equation 8]

$$y = r \times r\text{Step} \times \cos(t \times t\text{Step}) + Cy \quad (8)$$

[Equation 9]

$$x = r \times r\text{Step} \times \sin(t \times t\text{Step}) + Cx \quad (9)$$

In Equations (8) and (9), rStep denotes a step size in a moving radial direction and tStep denotes a step size in a declination direction. Furthermore, (Cy, Cx) are coordinates in the image serving as an origin of the polar coordinate transform, and are assumed herein as the center coordinates of the detection range 125.

Information stored in the storage portion 414 according to Example 2 will next be described. The parameters used in the image correction process such as the step size rStep in the moving radial direction and the step size tStep in the declination direction for use in the polar coordinate transform as well as the coefficients are stored in the storage portion 414 according to Example 2.

FIG. 12 is a view illustrating an example of a process of determining a state of a surface of the sample 111 executed by the image processing device 101 according to Example 2.

According to Example 2, after a process in Step S901, the image correction portion 1001 of the image processing device 101 reads the parameters from the storage portion 414, executes the image correction process, and calculates a corrected image (Step S1201). The image correction portion 1001 outputs the corrected image to the feature amount calculation portion 412.

Example 2 differs from Example 1 in that the feature amount calculation portion 412 executes the process described in Example 1 on the corrected image in Step S902. Processes in Steps S901 and S903 to S905 are identical to those according to Example 1.

While the polar coordinate transform has been described as an example of the image correction process, coordinate transform other than the polar coordinate transform, a process of normalizing an average value and a dispersion value of luminances, hues, and the like, a contrast enhancement process, an edge enhancement process, or a process of a combination of these processes may be performed.

According to Example 2, it is possible to achieve an improvement in image process accuracy, a reduction in computational complexity, and the like by executing the image correction process. It is possible, for example, to more accurately and more efficiently grasp the position of the object to be detected 115 with respect to the detection range 125 in the image.

Example 3

Example 3 differs from Example 1 in that coefficients are updated either periodically or successively using an image acquired at the time of analysis as a new learning image. Example 3 will be described hereinafter while mainly referring to differences from Example 1.

A system configuration according to Example 3 is identical to that according to Example 1. A hardware configuration of the image processing device 101 according to Example 3 is identical to that of the image processing device 101 according to Example 1. A software configuration of the image processing device 101 according to Example 3 partially differs from that according to Example 1. FIG. 13 is a view illustrating an example of the software configuration of the image processing device 101 according to Example 3. FIG. 14 is a view illustrating an example of a GUI displayed by the image processing device 101 according to Example 3.

Example 3 differs from Example 1 in that programs that realize a user operation input portion 1301, a learning portion 1302, and an image display portion 1303 are stored in the storage device 402. Example 3 also differs from Example 1 in that the image and the like acquired at the time of analysis are stored in the storage portion 414.

In Example 3, the image input portion 411 stores an input image in the storage portion 414. Furthermore, the sample state determination portion 413 stores an output signal in the storage portion 414. The storage portion 414 manages the image subjected to determination of the sample state and the output signal corresponding to the image in such a manner that the image corresponds to the output signal.

The image display portion 1303 generates display information for presenting an image selected by the learning portion 1302 to the user, and outputs the display information via the output device 404. A GUI 1400 illustrated in FIG. 14 is displayed on the basis of the output information.

The GUI 1400 includes an image display field 1401, a supervised signal selection field 1402, and a determination button 1403. It is noted that the GUI 1400 may include display fields other than those described above. The GUI 1400 may include, for example, a display field for presenting auxiliary information. In FIG. 14, a region indicating the detection range 125 is presented as auxiliary information.

The image display field 1401 is a field for displaying the image selected by the learning portion 1302. The supervised signal selection field 1402 is a field for selecting a supervised signal allocated to the image. A top radio button is a button for designating a supervised signal corresponding to the label 0. A middle radio button is a button for designating a supervised signal corresponding to the label 1. A bottom radio button is a button for designating a supervised signal corresponding to the label 2. The determination button 1403 is an operation button for outputting operation information including a value input to the supervised signal selection field 1402.

These are description of the GUI 1400. Description returns to FIG. 13.

The user operation input portion 1301 receives operation information output by operating the GUI 1400, and generates a supervised signal corresponding to the image presented on the GUI 1400. In a case, for example, in which the bottom radio button is operated in the supervised signal selection field 1402, the user operation input portion 1301 generates a supervised signal to which the label 2 is allocated.

The learning portion 1302 selects an image to be presented to the user from among the images stored in the storage portion 414 at the time of analysis, and outputs the selected image to the image display portion 1303. Furthermore, the learning Portion 1302 stores the selected image and the supervised signal input from the user operation input portion 1301 in the storage portion 414 in such a manner that the image corresponds to the supervised signal. Moreover, the learning portion 1302 updates the coefficients (determination model) stored in the storage portion 414 by executing machine learning using an image to which a supervised signal is allocated.

A flow of a process of determining the state of the sample surface 112 according to Example 3 is identical to the flow of the process according to Example 1. It is noted, however, that processes in Steps S901 and S904 partially differ from those according to Example 1. In Step S901, the image input portion 411 stores the image in the storage portion 414. In Step S904, the sample state determination portion 413 stores the output signal in the storage portion 414.

FIG. 15 is a flowchart for explaining an example of a process executed by the learning portion 1302 according to Example 3.

The learning portion 1302 selects an image to be presented to the user from among the images stored in the storage portion 414 either in a case in which a new image is acquired at the time of analysis or periodically (Step S1501). The learning portion 1302 outputs the selected image to the image display portion 1303.

Examples of an image selection method include a method for selecting an image for which a difference between a maximum likelihood and a minimum likelihood of the output signal calculated by the sample state determination portion 413 is the smallest.

The likelihoods are normalized by the softmax function so that a sum of all likelihoods is equal to 1.0. Owing to this, in a case of an image difficult to classify, the difference between the maximum likelihood and the minimum likelihood is small. In light of the above, presenting such an image to the user and inputting the image as a new learning image make it possible to efficiently improve determination accuracy.

Next, the learning portion 1302 receives a supervised signal from the user operation input portion 1301 (Step S1502). The learning portion 1302 allocates the supervised signal to the selected image and stores the resultant image in the storage portion 414 as a new learning image. In this way, the image processing device 101 can collect new learning images by repeatedly executing presenting the image and receiving the operation information.

Next, the learning portion 1302 determines whether the number of newly accumulated learning images is greater than a threshold (Step S1503). The process in Step S1503 is a process for detecting an opportunity of newly executing machine learning. Therefore, the other determination method may be used. For example, the machine learning may be executed either in a case in which an execution instruction is received from the user or in a case of passage of fixed time.

In a case of determining that the number of newly accumulated learning images is equal to or smaller than the threshold, the learning portion 1302 returns to Step S1501 and executes similar processes.

In a case of determining that the number of newly accumulated learning images is greater than the threshold, the learning portion 1302 executes the machine learning using the new learning image (Step S1504). It is noted that the machine learning is executed by a method similar to the process described in Example 1. New coefficients are calculated as a result of executing the machine learning.

Next, the learning portion 1302 determines whether to update the coefficients (Step S1505). Specifically, the learning portion 1302 evaluates the calculated coefficients in accordance with an arbitrary evaluation method, and determines whether to store the coefficients in the storage portion 414.

For example, the learning portion 1302 calculates determination accuracy of a correct answer-added image in a case of using the new coefficients in cooperation with the other configurations. In a case in which the determination accuracy is higher than a threshold, the learning portion 1302 determines to update the coefficients.

In a case of determining not to update the coefficients, the learning portion 1302 goes to Step S1507.

In a case of determining to update the coefficients, the learning portion 1302 stores the new coefficients in the storage portion 414 (Step S1506).

For example, the learning portion 1302 overwrites the newly calculated coefficients on the coefficients stored in the storage portion 414. Alternatively, the learning portion 1302 may store the unupdated coefficients and the newly calculated coefficients in the storage portion 414. In this alternative, the coefficients to be used may be able to be selected in response to user's operation.

In a case in which a determination result is NO in Step S1505 or after a process in Step S1506, the learning portion 1302 determines whether to end update of the coefficients (Step S1507).

In a case, for example, in which the determination accuracy is higher than the threshold or in which a user's end instruction is received, the learning portion 1302 determines to end update of the coefficients.

In a case of determining not to end update of the coefficients, the learning portion 1302 returns to Step S1501 and executes similar processes.

In a case of determining to end update of the coefficients, the learning portion 1302 ends the processes.

In the case of the update of the coefficients, the feature amount calculation portion 412 and the sample state determination portion 413 may immediately read the updated coefficients or read the updated coefficients in a case of actually performing processes.

While the learning portion 1302 uses the image acquired at the time of analysis as the new learning image, basic learning images to which the supervised signal is allocated may be stored in the storage portion 414 in advance.

While the learning portion 1302 automatically determines whether to update the coefficients on the basis of an evaluation result obtained using the arbitrary evaluation method, a determination method is not limited to this method. For example, the learning portion 1302 may present the evaluation result to the user and cause the user to determine whether to update the coefficients.

While the user manually selects the supervised signal allocated to the new learning image, a selection method is not limited to this method. For example, the learning portion 1302 or the like may determine the label corresponding to the output unit having the highest likelihood among the likelihoods included in the output signal as a provisional supervised signal, presents the provisional supervised signal and the image to the user, and cause the user to correct the provisional supervised signal. At this time, the following method may be applicable. In a case in which the provisional supervised signal has not been corrected for fixed time since the image is presented to the user, the learning portion 1302 adopts the provisional supervised signal as a proper supervised signal.

According to Example 3, the state of the sample surface 112 can be determined using the coefficients corresponding to the device and an environment by updating the coefficients; thus, it is possible to improve the determination accuracy.

The present invention can be realized by a program code of software that realizes the functions in the modes for carrying out the invention. In this case, a storage medium that records the program code is provided to the system or the device, and a computer (or CPU or MPU) of the system or the device reads the program code stored in the storage medium. In this case, the program code per ce read from the storage medium realizes the functions in the modes for carrying out the invention described above; thus, the program code per ce and the storage medium storing the program code configure the present invention. As the storage medium for supplying such a program code, a flexible disk, a CD-ROM, a DVD-ROM, a hard disk, an optical disk, a magneto-optical disk, a CD-R, a magnetic tape, a nonvolatile memory card, or a ROM, for example, is used.

Moreover, an OS (operating system) or the like running on the computer may execute part or all of actual processes on the basis of an instruction of the program code, and the functions in the modes for carrying out the invention described above may be realized by the processes. Moreover, after the program code read from the storage medium is written to a memory on the computer, a CPU of the computer may execute part or all of actual processes on the basis of an instruction of the program code, and the functions in the modes for carrying out the invention described above may be realized by the processes.

Furthermore, the program code of the software that realizes the functions in the modes for carrying out the invention may be distributed via a network, the program code may be thereby stored in storage means such as a hard disk or a memory of the computer or the device or in a storage medium such as a CD-RW or a CD-R, and at the time of use, the computer (or CPU or MPU) of the system or the device may read the program code stored in the storage means or the storage medium and execute the program code.

Finally, the processes and the technique described herein are essentially not associated with any specific device and can be implemented by any suitable combination of components. Furthermore, various types of general-purpose devices can be used in accordance with the methods described herein. It is often beneficial to construct a dedicated device to execute the steps of the methods described herein. Furthermore, various inventions can be created by appropriate combinations of a plurality of constituent elements disclosed in the modes for carrying out the invention. For example, several constituent elements may be deleted from all the constituent elements illustrated in the modes for carrying out the invention. Moreover, the constituent elements according to different modes for carrying out the invention may be combined as appropriate. While the present invention has been described in relation to specific examples, these examples are given not for limitation but for description in all viewpoints. A person having skill in the art can understand many combinations of hardware, software, and firmware suitable to carry out the present invention. The software described above can be implemented by, for example, a program or a script language in a wide range such as an assembler, C/C++, perl, Shell, PHP, and Java.

In the modes for carrying out the invention described above, control lines or information lines considered to be necessary for the description are illustrated and all the control lines or the information lines are not always illustrated in terms of a product. All the configurations may be mutually connected.

Additionally, other implementations of the present invention are obvious for a person having ordinary skill in the art from considerations of the specification of the present invention and the modes for carrying out the invention disclosed herein. Various aspects and/or components of the modes for carrying out the invention described above can be used either solely or by any combination.

The invention claimed is:

1. An apparatus for determining a state of a sample to be analyzed which is contained in a container, the apparatus comprising:
   a computation device; and
   a storage device connected to the computation device,
   wherein the computation device
      acquires an image of the sample,
      analyzes a position and a size of an object to be detected with respect to a detection range set in the image by using the image of the sample, and
      determines which of a first state in which the object to be detected is not present in the detection range, a second state in which the object to be detected at a first size of the object to be detected that does not affect analysis is present in the detection range, and a third state in which the object to be detected at a second size of the object to be detected that affects the analysis is present in the detection range, the state of the sample corresponds to, on a basis of a result of the analysis.

2. The apparatus according to claim 1,
   wherein the computation device
      acquires the image of the sample on an opening portion side of the container,
      calculates a value for evaluating the position and the size of the object to be detected with respect to the detection range, and
      determines the state of the sample on a basis of the calculated value.

3. The apparatus according to claim 2,
   wherein the storage device stores a determination model for determining the state of the sample, the determination model being generated by machine learning using a learning image to which a value indicating the state of the sample is applied.

4. The apparatus according to claim 3,
   wherein the computation device
      stores an image obtained by causing the state of the sample to correspond to the image of the sample in the storage device as a new learning image, and
      updates the determination model by executing machine learning using the new learning image.

5. The apparatus according to claim 4,
   wherein the computation device
      generates display information for displaying the image of the sample, and
      stores an image obtained by causing the state of the sample designated on a basis of the display information to correspond to the image of the sample in the storage device as the new learning image.

6. The apparatus according to claim 2,
   wherein the computation device
      executes an arbitrary image correction process on the image of the sample, and
      analyzes the position and the size of the object to be detected with respect to the detection range by using the image of the sample on which the image correction process is executed.

7. The apparatus according to claim 2,
   wherein the apparatus is connected to an acquisition device having an acquisition mechanism for collecting the sample, and
   wherein the detection range is a range about a position where the acquisition mechanism is in contact with a surface of the sample when the acquisition device acquires the sample.

8. A method for determining a state of a sample to be executed, by an apparatus which determines the state of the sample to be analyzed, the sample being contained in a container and includes a computation device and a storage device connected to the computation device, the method for determining the state of the sample comprising:
   a first step of acquiring an image of the sample, by the computation device;
   a second step of analyzing a position and a size of an object to be detected with respect to a detection range set in the image by using the image of the sample, by the computation device; and
   a third step of determining which of a first state in which the object to be detected is not present in the detection range, a second state in which the object to be detected at a first size of the object to be detected that does not affect analysis is present in the detection range, and a third state in which the object to be detected at a second size of the object to be detected that affects the analysis is present in the detection range, the state of the sample corresponds to, on a basis of a result of the analysis, by the computation device.

9. The method for determining a state of a sample according to claim 8,
   wherein, in the first step, the computation device acquires the image of the sample on an opening portion side of the container,
   wherein, in the second step, the computation device calculates a value for evaluating the position and the size of the object to be detected with respect to the detection range, and
   wherein, in the third step, the computation device determines the state of the sample on a basis of the calculated value.

10. The method for determining a state of a sample according to claim 9,
    wherein the storage device stores a determination model for determining the state of the sample, the determination model being generated by machine learning using a learning image to which a value indicating the state of the sample is applied.

11. The method for determining a state of a sample according to claim 10, comprising:
    a step of generating display information for displaying the image of the sample, by the computation device;
    a step of storing an image obtained by causing the state of the sample designated on a basis of the display information to correspond to the image of the sample in the storage device as a new learning image, by the computation device; and
    a step of updating the determination model by executing machine learning using the new learning image, by the computation device.

12. An analysis system for analyzing a sample, comprising:
- an image acquisition device that acquires an image of the sample contained in a container;
- an image processing device that determines a state of the sample contained in the container by analyzing the image;
- an acquisition device that acquires the sample from the container; and
- an analysis device that analyzes the sample,
- wherein the image acquisition device acquires the image of the sample and outputs the image to the image processing device,
- wherein the image processing device
  - analyzes a position and a size of an object to be detected with respect to a detection range set in the image by using the image of the sample,
  - determines which of a first state in which the object to be detected is not present in the detection range, a second state in which the object to be detected at a first size of the object to be detected that does not affect analysis is present in the detection range, and a third state in which the object to be detected at a second size of the object to be detected that affects the analysis is present in the detection range, the state of the sample corresponds to, on a basis of a result of the analysis, and
  - outputs information associated with the state of the sample, as information for controlling the acquisition device.

13. The analysis system according to claim 12,
wherein the image acquisition device acquires an image of the sample on an opening portion side of the container,
wherein the image processing device
- calculates a value for evaluating the position and the size of the object to be detected with respect to the detection range, and
- determines that the state of the sample on a basis of the calculated value.

14. The analysis system according to claim 13,
wherein the image processing device holds a determination model for determining the state of the sample, the determination model being generated by machine learning using a learning image to which a value indicating the state of the sample is applied.

* * * * *